(12) United States Patent
Norris et al.

(10) Patent No.: US 9,610,183 B2
(45) Date of Patent: Apr. 4, 2017

(54) FRICTION FIBER SLEEVE RETRACTION SYSTEM

(71) Applicant: W. L. Gore & Associates, Inc., Newark, DE (US)

(72) Inventors: Patrick M. Norris, Bellemont, AZ (US); Matthew G. Sondreaal, Phoenix, AZ (US)

(73) Assignee: W.L. Gore & Associates, Inc., Newark, DE (US)

( * ) Notice: Subject to any disclaimer, the term of this patent is extended or adjusted under 35 U.S.C. 154(b) by 120 days.

(21) Appl. No.: 14/076,399

(22) Filed: Nov. 11, 2013

(65) Prior Publication Data
US 2014/0135894 A1    May 15, 2014

Related U.S. Application Data

(60) Provisional application No. 61/725,363, filed on Nov. 12, 2012.

(51) Int. Cl.
*A61F 2/06* (2013.01)
*A61F 2/966* (2013.01)
*A61F 2/962* (2013.01)
*A61F 2/97* (2013.01)

(52) U.S. Cl.
CPC .............. *A61F 2/966* (2013.01); *A61F 2/962* (2013.01); *A61F 2/97* (2013.01); *A61F 2002/9665* (2013.01)

(58) Field of Classification Search
CPC .. A61F 2/95; A61F 2/962; A61F 2/966; A61F 2/97; A61F 2002/9665
See application file for complete search history.

(56) References Cited

U.S. PATENT DOCUMENTS

| 6,146,389 | A | * | 11/2000 | Geitz ........................ A61F 2/95 600/121 |
| 6,514,281 | B1 | * | 2/2003 | Blaeser et al. ............... 623/1.12 |
| 6,733,520 | B2 | | 5/2004 | Yang et al. |
| 8,500,789 | B2 | | 8/2013 | Wuebbeling et al. |
| 2003/0004561 | A1 | | 1/2003 | Bigus et al. |
| 2006/0015171 | A1 | * | 1/2006 | Armstrong .................. 623/1.12 |
| 2007/0027522 | A1 | | 2/2007 | Chang et al. |
| 2007/0260302 | A1 | | 11/2007 | Igaki |
| 2010/0049293 | A1 | | 2/2010 | Zukowski et al. |
| 2012/0065644 | A1 | * | 3/2012 | Ng et al. ....................... 606/108 |
| 2012/0130475 | A1 | | 5/2012 | Shaw |
| 2012/0165915 | A1 | | 6/2012 | Melsheimer et al. |

FOREIGN PATENT DOCUMENTS

| EP | 0 732 087 | 9/1996 |
| WO | 2013/137978 | 9/2013 |

OTHER PUBLICATIONS

International Search Report for PCT/US2013/069651 mailed Feb. 11, 2014.

* cited by examiner

*Primary Examiner* — Melanie Tyson

(57) ABSTRACT

An implantable system for endoluminal delivery of expandable devices having one or more sleeves and one or more sleeve pull back lines. The sleeve pull back lines enable retraction of the one or more sleeves, with various benefits resulting therefrom.

20 Claims, 2 Drawing Sheets

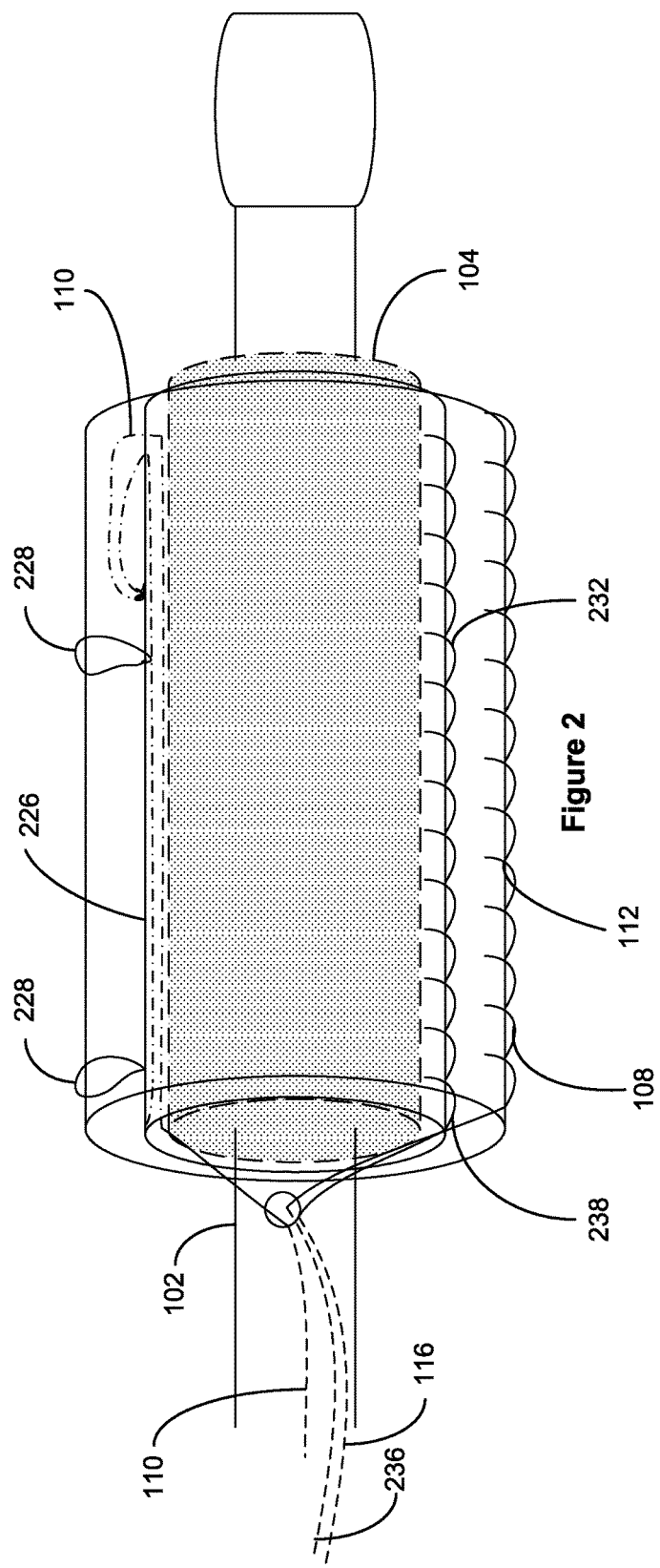

FRICTION FIBER SLEEVE RETRACTION SYSTEM

BACKGROUND

Field

The present disclosure relates generally to transcatheter delivery and remote deployment of endoluminal devices and, more particularly, to endoluminal devices having one or more sleeves with one or more pull back lines for retracting the one or more of the sleeves.

Discussion of the Related Art

Endoluminal devices are frequently used to treat the vasculature of human patients. Such devices often include a sleeve. It may be desirable to at least partially retract a sleeve, such as, a sleeve configured to remain in situ after deployment of the underlying endoluminal device, for example, to prevent inadvertent obstruction of a branch vessel by the sleeve. Thus, there is a need for systems that provide such sleeve retraction characteristics.

BRIEF DESCRIPTION OF THE DRAWINGS

The accompanying drawings are included to provide a further understanding of the disclosure and are incorporated in and constitute a part of this specification, illustrate embodiments of the disclosure, and together with the description, serve to explain the principles of the disclosure, wherein:

FIG. 2 illustrates a sleeve retraction system.

DETAILED DESCRIPTION OF THE ILLUSTRATED EMBODIMENTS

Figure 1:
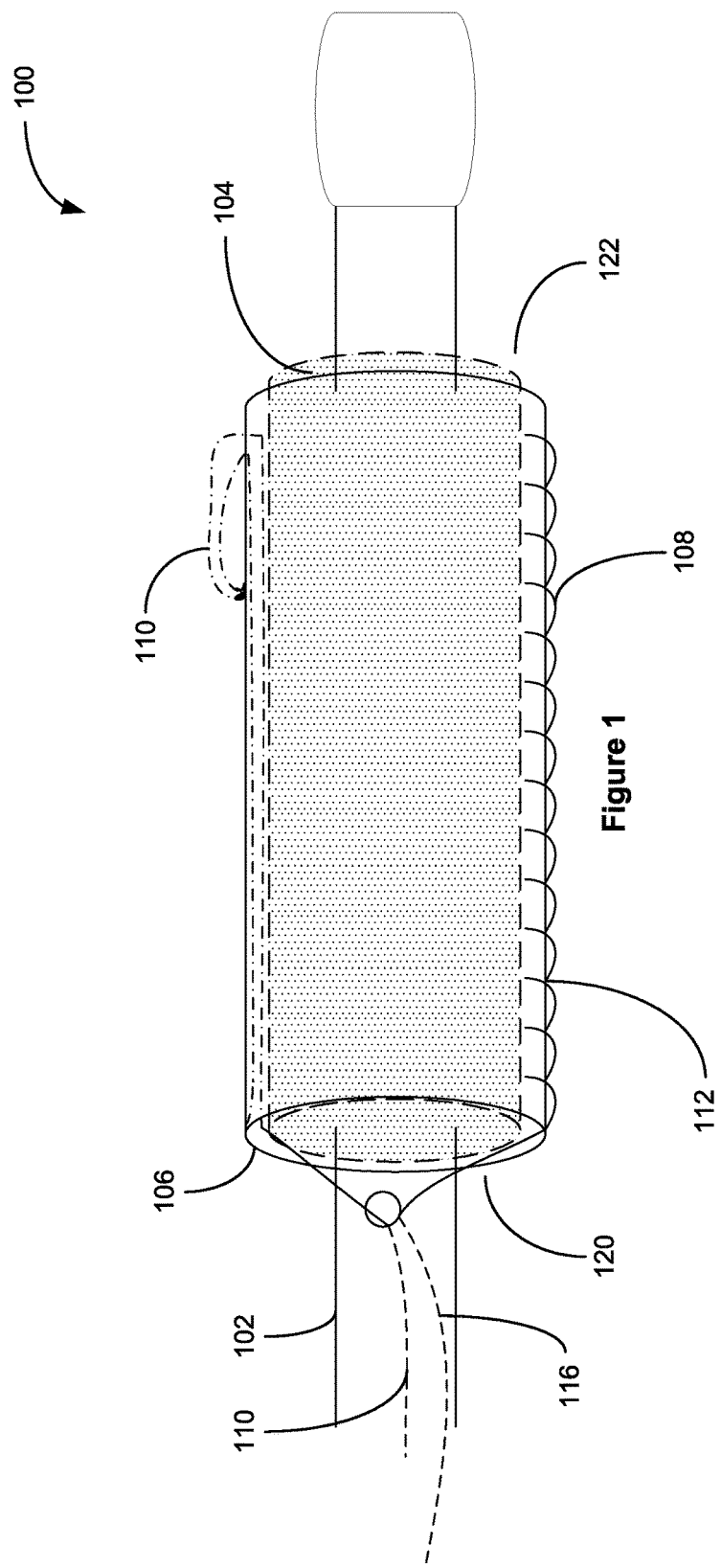
FIG. 1 illustrates a sleeve retraction system.

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure can be described in connection with various principles and beliefs, the present disclosure should not be bound by theory.

Endoluminal devices are frequently used to treat the vasculature of human patients. These treatments or procedures are commonly referred to as intraluminal or endovascular procedures. Systems for delivering such endoluminal devices often include one or more constraining sleeves.

For the purposes of the disclosure, the term "constrain" may mean (i) to limit the expansion, either through self-expansion or assisted by a device, of the diameter of an endoluminal device or (ii) to cover or surround but not otherwise restrain an endoluminal device (e.g., for storage or biocompatibility reasons and/or to provide protection to the endoluminal device and/or the vasculature).

Throughout this specification and in the claims, the term "distal" refers to a location, or a portion of an endoluminal device (such as a stent-graft), that is further downstream with respect to blood flow than another portion of the device. Similarly, the term "distally" refers to the direction of blood flow or further downstream in the direction of blood flow.

The term "proximal" refers to a location, or a portion of an endoluminal device, that is further upstream with respect to blood flow than another portion of the device. Similarly, the term "proximally" refers to the direction opposite to the direction of blood flow or upstream from the direction of blood flow.

With further regard to the terms proximal and distal, and because the present disclosure is not limited to peripheral and/or central approaches, this disclosure should not be narrowly construed with respect to these terms. Rather, the devices and methods described herein can be altered and/or adjusted relative to the anatomy of a patient.

With reference to FIG. 1, systems of the present disclosure comprise a catheter shaft 102 and endoluminal device 104. Endoluminal device 104 can be surrounded by a constraining sleeve 106, which constrains endoluminal device 104 in a reduced diameter configuration.

Endoluminal device 104 can comprise, for example, stents, grafts, filters, valves, anchors, occluders, and other implantable devices, and also includes all of the foregoing constrained in one or more sleeves.

As illustrated in FIG. 1, endoluminal device 104 can be surrounded by one or more constraining sleeves, such as constraining sleeve 106. In various embodiments, constraining sleeve 106 maintains endoluminal device 104 in a reduced diameter, such as a delivery diameter in which the diameter of endoluminal device 104 is reduced sufficiently for delivery of the device through the vasculature and to the treatment area of a patient.

As used herein, the term "sleeve" refers to a primary, secondary, tertiary, etc., sleeve, sheath, or the like, that constrains an endoluminal device in a collapsed configuration for endoluminal delivery of the device to a treatment portion of the vasculature of a patient.

In various embodiments, constraining sleeve 106 comprises a polymeric material, such as, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. Other embodiments for the constraining sleeve 106 material can include high strength polymer fibers such as ultra high molecular weight polyethylene fibers (e.g., Spectra®, Dyneema Purity®, etc.) or aramid fibers (e.g., Technora®, etc.). Constraining sleeve 106 may include a bioactive agent. Any sleeve which may be used to constrain an endoluminal device is in accordance with the present disclosure.

With reference to FIG. 2, catheter assembly 100 can comprise a first constraining sleeve 106 and a second constraining sleeve 226. In such configurations, first constraining sleeve 106 concentrically surrounds both second constraining sleeve 226 and endoluminal device 104. First constraining sleeve 106 and second constraining sleeve 226 can be configured to maintain endoluminal device in two different reduced diameter configurations.

For example, as described in relation to FIG. 1, first constraining sleeve 106 can be configured to maintain endoluminal device 104 in a configuration with a diameter suitable for delivery through the vasculature and to the treatment area of a patient.

In various embodiments, second constraining sleeve 226 can be configured to maintain endoluminal device 104 in a reduced diameter configuration, wherein the diameter is less than that of the unconstrained implant and greater than that of the delivery configuration. For example, in various embodiments, second constraining sleeve 226 constrains endoluminal device 104 in an intermediate configuration. In the intermediate configuration, the diameter of endoluminal device 104 is constrained in a diameter smaller than the expanded configuration and larger than the collapsed configuration. For example, the diameter of endoluminal device 104 in the intermediate configuration can be about 50% of the diameter of endoluminal device 104 in the expanded configuration. However, any diameter of the intermediate configuration which is less than the diameter of the expanded configuration and larger than the delivery or collapsed configuration is within the scope of the disclosure.

Upon disengagement or removal of first constraining sleeve 106, endoluminal device 104 is capable of expanding to the intermediate diameter configuration, as constrained by second constraining sleeve 226. For example, endoluminal device 104 can be expanded from the collapsed configuration to the intermediate configuration once expandable implant 104 has been delivered near the treatment area of the vasculature of a patient. The intermediate configuration can, among other things, assist in properly orienting and locating the expandable implant within the treatment area of the vasculature.

In various embodiments, catheter assembly 100 can further comprise a coupling member 108. In various embodiments, the coupling member 108 is suitably configured to couple adjacent parallel edges of the constraining sleeve 106 by engaging a plurality of holes 112 formed in the constraining sleeve 106. As used herein, the term "coupling" refers to any coupling, stitch (e.g., a chain stitch), thread, weave pattern, etc., which can be used to close the constraining sleeve 106.

In various embodiments, coupling member 108 is attached or integral to a deployment line 116. In such configurations, coupling member 108 is released by applying tension to the deployment line 116, allowing sleeve 106 to open.

Coupling member 108 and deployment line 116 can comprise, for example, any type of string, cord, thread, fiber, or wire, can comprise metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol; and high strength polymer fibers such as ultra high molecular weight polyethylene fibers (e.g., Spectra®, Dyneema Purity®, etc.) or aramid fibers (e.g., Technora®, etc.).

With reference to FIG. 2, once endoluminal device 104 is properly located and oriented within the treatment area of the patient, second constraining sleeve 226 can be removed or disengaged from endoluminal device 104. Endoluminal device 104 can then be fully deployed within the treatment area. Similarly to first constraining sleeve 106, second constraining sleeve 226 can be held closed around endoluminal device 104 by a second coupling member 238 that is engaged with a second plurality of holes 232. Second coupling member 238 can be engaged with or integral to second deployment line 236. In such configurations, second constraining sleeve 226 can be opened by applying sufficient tension to second deployment line 236.

In various embodiments, catheter assembly 100 further comprises a sleeve pull back line 110. As illustrated in FIGS. 1 and 2, sleeve pull back line 110 is engaged with first constraining sleeve 106 or second constraining sleeve 226. Sleeve pull back line 110 extends from distal end 120 of endoluminal device 104 towards proximal end 122.

As illustrated in FIG. 1, in embodiments with a single sleeve, sleeve pull back line 110 travels between endoluminal device 104 and first constraining sleeve 106. Sleeve pull back line 110 can travel from the distal end 120 to the proximal end 122 of endoluminal device 104, and out of first constraining sleeve 106. In such configurations, sleeve pull back line 110 can generate a frictional force at or near the proximal end of the sleeve, thereby assisting in pulling first constraining sleeve 106 back from proximal end 122.

In various embodiments, sleeve pull back line 110 can extend beyond the proximal end of endoluminal device 104 and enter first constraining sleeve 106. Sleeve pull back line 110 can, for example, tie to itself to form a knot at or near the proximal end of endoluminal device 104. In other embodiments, sleeve pull back line 110 can enter first constraining sleeve 106 and travel back towards distal end 120 of endoluminal device.

As illustrated in FIG. 2, in embodiments with two sleeves, sleeve pull back line 110 can, for example, travel between second constraining sleeve 226 and endoluminal device 104. In such configurations, similarly to those described in relation to FIG. 1, sleeve pull back line 110 travels between endoluminal device 104 and second constraining sleeve 226. Sleeve pull back line 110 can travel from the distal end 120 to the proximal end 120 of endoluminal device 104, and out of second constraining sleeve 226. In various embodiments, sleeve pull back line 110 can extend beyond the proximal end of endoluminal device 104 and enter second constraining sleeve 226. Sleeve pull back line 110 can, for example, tie to itself to form a knot at or near the proximal end of endoluminal device 104. In other embodiments, sleeve pull back line 110 can enter second constraining sleeve 226 and travel back towards distal end 120 of endoluminal device.

Similar to coupling member 108 and deployment line 116, sleeve pullback line 110 can comprise, for example, any type of string, cord, thread, fiber, or wire, can comprise metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol; and high strength polymer fibers such as ultra high molecular weight polyethylene fibers (e.g., Spectra®, Dyneema Purity®, etc.) or aramid fibers (e.g., Technora®, etc.).

In various embodiments, deployment line 116 and the sleeve pull back line 110 can be pulled simultaneously by an operator. For example, with reference to FIG. 2, tension can be applied to second deployment line 236 to remove second coupling member 238 from second plurality of holes 232 and release second constraining sleeve 226. At the same time, tension can be applied to sleeve pull back line 110, for example, to retract second constraining sleeve 226 as it is released from surrounding endoluminal device 104.

In other embodiments, sleeve retraction can cease shortly thereafter while the device deployment continues. In yet other embodiments, deploying the underlying device can begin prior to sleeve retraction. In still other embodiments, deploying the underlying device can begin after sleeve retraction.

In various embodiments, and with reference to FIG. 2, catheter assembly 100 can further comprise one or more sleeve coupling loops. In embodiments with two sleeves, such as first constraining sleeve 106 and second constraining sleeve 226, one or more sleeve coupling loops can releasably connect the two constraining sleeves, so that retraction of one sleeve simultaneously retracts the other sleeve. For example, one sleeve coupling loop 228 can be located near the distal end of first constraining sleeve 106 and second constraining sleeve 226, and another near the proximal end. As tension is applied to sleeve pull back line 110 to retract second constraining sleeve 226, sleeve coupling loops 228 act to retract first constraining sleeve 106 simultaneously. Any number and position of sleeve coupling loops is within the scope of the present disclosure.

Although described in regards to specific examples, any configuration of one or more sleeves, one or more sleeve pull back lines, and endoluminal devices is within the scope of the present disclosure. Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. An implantable system comprising:
    an endoluminal device having a distal end and a proximal end;
    a flexible constraining sleeve surrounding the endoluminal device;
    a coupling member releasably coupled to the constraining sleeve to retain the endoluminal device toward a delivery configuration suitable for endoluminal delivery; and
    a sleeve pull back line engaged with the constraining sleeve, the sleeve pull back line disposed between the constraining sleeve and the endoluminal device and extending from the distal end of endoluminal device towards and beyond the proximal end, towards the distal end exterior to the constraining sleeve, back towards the proximal end exterior to the constraining sleeve, and back towards the distal end of the endoluminal device between the constraining sleeve and the endoluminal device to engage the flexible constraining sleeve, the sleeve pull back line being configured to generate frictional force between the sleeve pull back line and the constraining sleeve in response to applying tension to the sleeve pull back line thereby displacing a portion of the constraining sleeve relative to the endoluminal device.

2. The implantable system of claim 1, wherein the sleeve pull back line engages a proximal end of the constraining sleeve.

3. The implantable system of claim 2, wherein the sleeve pull back line doubles back after engaging the proximal end of the constraining sleeve and engages a distal end of the constraining sleeve.

4. The implantable system of claim 1, wherein the coupling member engages a plurality of holes along opposing and parallel edges of the constraining sleeve, and the sleeve pull back line comprises a knot at or near a proximal end of the endoluminal device.

5. The implantable system of claim 4, wherein tension applied to the coupling member releases the constraining sleeve and allows the endoluminal device to expand.

6. The implantable system of claim 4, wherein the coupling member and the sleeve pull back line are configured to have tension applied to the coupling member and the sleeve pull back line simultaneously.

7. The implantable system of claim 4 wherein the constraining sleeve is a first constraining sleeve, and further comprising a second constraining sleeve, wherein the first constraining sleeve concentrically surrounds the second constraining sleeve, and wherein the sleeve pull back line is disposed between the second constraining sleeve and the endoluminal device.

8. The implantable system of claim 7, further comprising at least one sleeve coupling loop, wherein the sleeve coupling loop removably couples the first constraining sleeve and the second constraining sleeve.

9. The implantable system of claim 8, comprising a first coupling loop and a second coupling loop, wherein the first coupling loop is oriented near a proximal end of the endoluminal device, and the second coupling loop is oriented near a distal end of the endoluminal device.

10. The implantable system of claim 7, wherein the sleeve pull back line is moveably engaged to one of the first constraining sleeve and second constraining sleeve through a hole.

11. The implantable system of claim 7 wherein sleeve pull back line is disposed between the constraining sleeve and the endoluminal device and extending from the distal end of endoluminal device towards and beyond the proximal end, towards the distal end between the first constraining sleeve and the second constraining sleeve, back towards the proximal end between the first constraining sleeve and the second constraining sleeve, and back towards the distal end of the endoluminal device between the constraining sleeve and the endoluminal device to engage the flexible constraining sleeve.

12. The implantable system of claim 1, wherein the sleeve pull back line is removeable.

13. The implantable system of claim 1, wherein the endoluminal device is one of a stent, graft, filter, and valve.

14. The implantable system of claim 1 wherein the constraining sleeve is comprised of expanded polytetrafluoroethylene.

15. The implantable system of claim 7 wherein the second constraining sleeve is comprised of expanded polytetrafluoroethylene.

16. The implantable system of claim 1, wherein the sleeve pull back line comprises a knot between a first portion extending towards the distal end exterior to the constraining sleeve and a second portion extending back towards the proximal end exterior to the constraining sleeve.

17. An implantable system comprising:
    an endoluminal device having a distal end and a proximal end;
    a flexible constraining sleeve surrounding the endoluminal device;
    a coupling member releasably coupled to the constraining sleeve to retain the endoluminal device toward a delivery configuration suitable for endoluminal delivery; and
    a sleeve pull back line engaged with the constraining sleeve, the sleeve pull back line disposed between the constraining sleeve and the endoluminal device and extending from the distal end of endoluminal device towards and beyond the proximal end, towards the distal end exterior to the constraining sleeve, back towards the proximal end exterior to the constraining sleeve, and back towards the distal end of the endoluminal device between the constraining sleeve and the endoluminal device to engage the flexible constraining sleeve.

18. The implantable system of claim 17 wherein the constraining sleeve is a first constraining sleeve, and further comprising a second constraining sleeve, wherein the first constraining sleeve concentrically surrounds the second constraining sleeve, and wherein the sleeve pull back line is disposed between the second constraining sleeve and the endoluminal device.

19. The implantable system of claim 18 wherein sleeve pull back line is disposed between the constraining sleeve and the endoluminal device and extending from the distal end of endoluminal device towards and beyond the proximal end, towards the distal end between the first constraining sleeve and the second constraining sleeve, back towards the proximal end between the first constraining sleeve and the second constraining sleeve, and back towards the distal end of the endoluminal device between the constraining sleeve and the endoluminal device to engage the flexible constraining sleeve.

20. The implantable system of claim 17, wherein the sleeve pull back line comprises a knot between a first portion extending towards the distal end exterior to the constraining sleeve and a second portion extending back towards the proximal end exterior to the constraining sleeve.

\* \* \* \* \*